(12) United States Patent
Fauth

(10) Patent No.: US 12,142,950 B2
(45) Date of Patent: Nov. 12, 2024

(54) CAPACITIVE SHIELD FOR CHARGER ARTIFACT REDUCTION FOR IMPLANTS

(71) Applicant: Neuralink Corp., Fremont, CA (US)

(72) Inventor: Lucia Fauth, Menlo Park, CA (US)

(73) Assignee: Neuralink Corp., Fremont, CA (US)

( * ) Notice: Subject to any disclaimer, the term of this patent is extended or adjusted under 35 U.S.C. 154(b) by 496 days.

(21) Appl. No.: 17/553,364

(22) Filed: Dec. 16, 2021

(65) Prior Publication Data

US 2023/0198316 A1 Jun. 22, 2023

(51) Int. Cl.
*H02J 50/70* (2016.01)
*A61N 1/372* (2006.01)
*A61N 1/378* (2006.01)
*H02J 50/00* (2016.01)
*H02J 50/10* (2016.01)

(52) U.S. Cl.
CPC .......... *H02J 50/70* (2016.02); *A61N 1/37229* (2013.01); *A61N 1/3787* (2013.01); *H02J 50/005* (2020.01); *H02J 50/10* (2016.02); *H02J 2310/23* (2020.01)

(58) Field of Classification Search
CPC ........ H02J 2310/23; H02J 50/12; H02J 50/23; H02J 50/27; H02J 50/10; H02J 50/70; H02J 50/005; A61N 1/3787; A61N 1/37229

See application file for complete search history.

(56) References Cited

U.S. PATENT DOCUMENTS

| | | | |
|---|---|---|---|
| 8,321,028 B1* | 11/2012 | Thenuwara | A61N 1/37229 607/36 |
| 2015/0025613 A1* | 1/2015 | Nyberg, II | A61N 1/37229 29/601 |

OTHER PUBLICATIONS

Liao, et al., EMI Considerations for Inductive Sensing, Application Report, Feb. 2017, pp. 1-6, SNOA962, Texas Instruments.

* cited by examiner

*Primary Examiner* — David V Henze-Gongola
(74) *Attorney, Agent, or Firm* — Kilpatrick Townsend & Stockton LLP

(57) ABSTRACT

A set of shielded coils for wireless power transmission into a medical implant is described in which the external, power transmission coil is blocked at least on one side by a shield with a broken ring and radial fingers while the power receiver coil inside the medical implant is surrounded by a shield having a broken ring connecting radial fingers and ribs around its circumference. The finger and rib configurations minimizes eddy currents in the shields. A ground plane of the implant's internal circuitry, which is within the shield along with the receiver coil, can cap off the cupped receiver shield to form a Faraday cage with it. The metal or other conductive shielding prevents large electric fields from the coils from penetrating into the tissue of the subject while simultaneously allowing magnetic fields inductively couple the coils for charging. An implant with sensitive electrodes that measure minute voltages from a brain or other tissues is protected from capacitively driven voltage swings or other transients during charging.

20 Claims, 8 Drawing Sheets

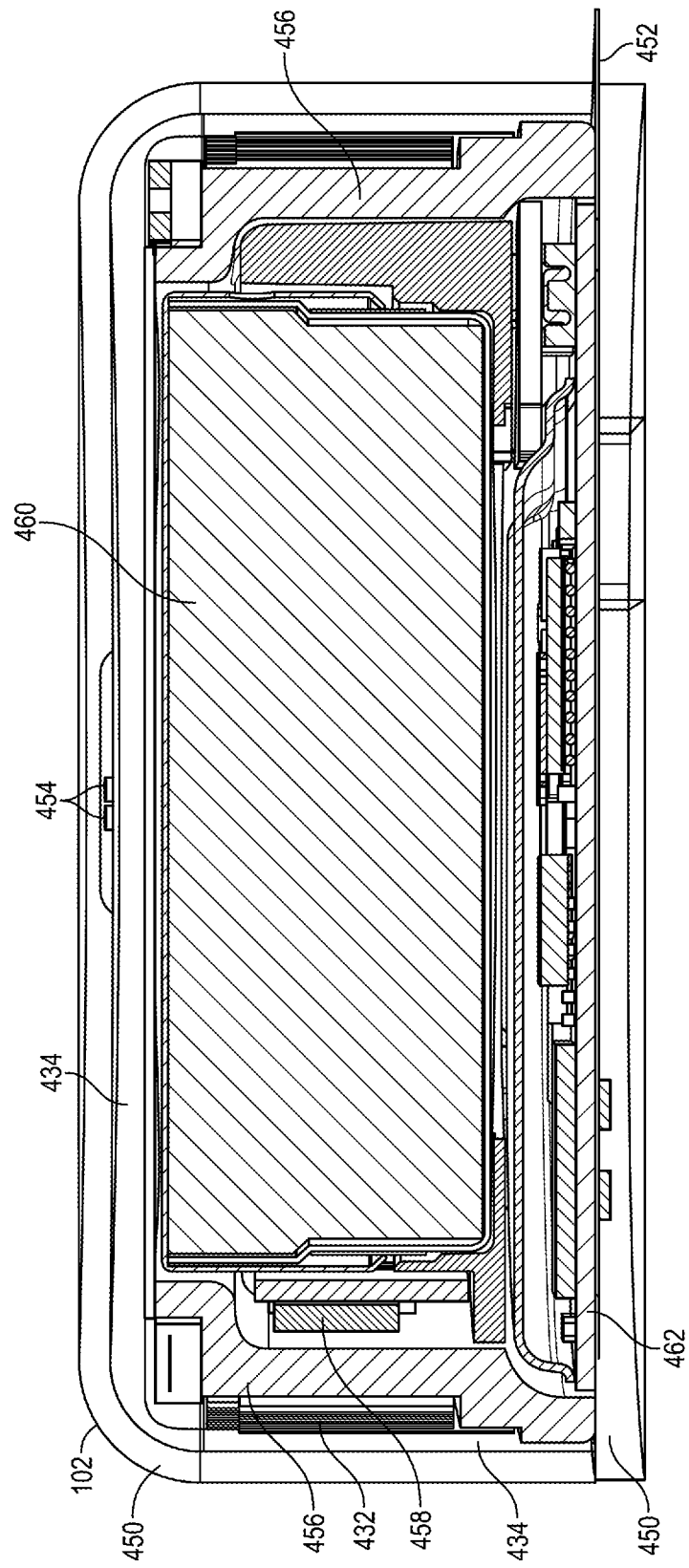

CAPACITIVE SHIELD FOR CHARGER ARTIFACT REDUCTION FOR IMPLANTS

CROSS-REFERENCES TO RELATED APPLICATIONS

NOT APPLICABLE

STATEMENT AS TO RIGHTS TO INVENTIONS MADE UNDER FEDERALLY SPONSORED RESEARCH AND DEVELOPMENT

NOT APPLICABLE

BACKGROUND

1. Field of the Invention

Embodiments of the present invention generally relate to circuit arrangements or systems for wireless supply or distribution of electric power, including the reduction of electric leakage fields. More specifically, they relate to a coil shield system having eddy current-minimizing fingered conductors that block electric fields on a transmitter coil and enclose electric fields on a receiver coil that may be immersed in tissue.

2. Description of the Related Art

Medical devices for implantation into biological tissue often require electrical power for electronics inside them. Such electronics can include sensors, stimulators, processors, memory, and associated components. Like any other electronics, they require electrical power. Battery power is preferred in order to maintain mobility of the subject.

Batteries operating over long periods of time need to be recharged. Wireless charging avoids the need for cables that transit through the skin, avoiding infection pathways and mechanical issues with wires getting pushed, pulled, or pinched. One technique of wireless charging that has found favor in consumer electronics is through resonant inductive coupling.

Resonant inductive coupling between a transmitter coil and receiver coil is an efficient way to transfer power over short distances, such as between an external charger and a subcutaneous implant. Such coupling employs magnetic fields. To work, an alternating current (AC) is driven in the transmitter coil, which causes a magnetic ("B") field in the volume around it. When close enough to the receiver coil, the magnetic field passes through it and induces current in the receiver coil. The induced current, oscillating at the same frequency as the alternating current in the transmitter coil and at a resonant frequency of the receiver coil circuit, is rectified to direct current (DC). The direct current can be used to stimulate electrodes, power electronics, charge a battery, or other uses.

Magnetic fields are effective for near-field charging electronic toothbrushes, smart phones, and full size electric vehicles. They do not interact with nonmetals or nonmagnetic materials, such as biological tissue, and so are employed in some medical devices.

"Biological tissue" includes any collection of cells of a multi-cellular organism or products from said collections of cells that are integrated for use by the cells. This includes organs, vasculature, epidermis, fat, muscle, bones, and as otherwise known in the art.

Unfortunately, the current in the transmitter coil not only emits a magnetic field but also an electric ("E") field. Biological tissue, such as that in a brain, is quite conductive and affected by electric fields. Because the tissue is conductive, the electric field from the transmitter coil induces currents in it.

Further, the receiver coil, inside the implant, also creates an electric field from its induced current. That is, the flow of electrons induced into motion around the receiver coil causes its own electric field. This electric field can be thought of as distinct from that of the transmitter coil, although the distinction does not necessarily matter in this discussion. That fact is that the electric field in the receiver coil also induces currents in the tissue. And the receiver coil, being inside the implant and surrounded by tissue, may have an even large effect on the tissue than the transmitter coil.

The common term in the art for electric fields causing unintended currents in tissue (or any other conductive material) is "parasitic capacitance." If kept small enough in medical device chargers, the minor currents caused by parasitic capacitance in the surrounding tissue are safe for the tissue and have little-to-no effect on a medical device. For example, tens of volts on the coils may cause only a couple of hundred millivolts in the tissue. This may be acceptable for temporary periods of charging and well insulated medical devices.

However, this is not acceptable for medical devices whose very purpose is to measure small voltages in the tissue. For example, a neural device implanted in the brain may measure neural signals on the order of microvolts ($\mu V$). Oscillations of merely a few millivolts within tissue may cause too much eddy current noise to detect signals on the order of $\mu V$.

There is a need in the art for wireless charging and other near-field electrical power transfer that minimizes their effect on tissue, especially in applications where a medical device is measuring small electrical voltages or currents in the very same tissue.

BRIEF SUMMARY

Generally, a transmitter coil in a wireless charger is capacitively shielded on a side facing its target device by a conductive screen comprising a split metal ring and radial fingers that are grounded. This inhibits an electric field on that side of the coil from penetrating tissue around the target device. Meanwhile, a receiver coil in the target device, an implant, is capacitively shielded all around by another split metal ring (annulus), strips, and ribs that are connected to a common implant ground. The implant ground is separate from any precision sensor grounds for electronics within the device. The receiver shield suppresses an electric field emanating from the receiver coil, through which currents are induced by the transmitter coil's magnetic field. A ground plane for the electronics can cap off one side of the shield, forming a full Faraday cage around the receiver coil and preventing capacitive coupling to surrounding tissue.

This configuration can be especially supportive of implants that measure extremely small voltages or currents, e.g. microvolt or microampere ($\mu A$), in the surrounding tissue. Such implants can employ electrodes that project into tissue and feed to high-gain amplifiers and analog-to-digital (A2D) converters.

Some embodiments of the present invention are related to a capacitively shielded magnetic inductive coupling apparatus for medical implants. The apparatus includes a transmitter coil, a transmitter shield spanning a full diameter of the transmitter coil, the transmitter shield including a conductive ring having a break so as to prevent a closed 360 degree loop around the ring, conductive fingers projecting radially outward or inward from the ring, and a transmitter ground connection for connecting the ring and the fingers to a transmitter ground. The apparatus also includes a receiver coil within an implant device and configured to inductively couple through magnetic fields with the transmitter coil, and a receiver shield cupping around the receiver coil, the receiver shield including a conductive annulus having a break so as to prevent a 360 degree closed loop around the annulus, conductive strips projecting radially outward or inward from the annulus, conductive ribs projecting perpendicularly around a circumference of the annulus, and a receiver ground connection connecting the annulus, strips, and ribs to an implant ground for the implant device. The transmitter shield and the receiver shield are configured to curtail capacitive coupling through electric fields to tissue around the implant device.

The apparatus can also include an electrode input that connects from outside to inside the implant device. It can include a ground plane over an end of the cupped receiver shield and forming a Faraday cage with the conductive annulus, the conductive strips, and the conductive ribs of the receiver shield. The apparatus can further include a polymeric, cylindrical housing around the receiver shield and the ground plane. The apparatus can include a round of ferrite, the receiver coil wrapped around a diameter of the round of ferrite.

The apparatus can include a patch antenna centered within the conductive annulus of the receiver shield, the patch antenna configured for data communications.

The conductive fingers of the transmitter shield can project only outward from the ring. The annulus can be in a plane parallel to the receiver coil. The magnetic inductive coupling apparatus can be a charger system, and the apparatus can further include a recharging circuit configured to receive power from the receiver coil and charge a battery. The apparatus can include insulation within the break of the conductive ring or the break of the conductive annulus. The conductive annulus of the receiver coil can be made from a biocompatible metal selected from the group consisting of gold, platinum, silver, tantalum, and titanium. The implant device can be implanted within tissue of a subject.

Some embodiments are related to a method of capacitively shielding a magnetic inductive coupling apparatus for medical implants. The method can include transmitting electromagnetic energy from a transmitter coil, inhibiting an electric field of the electromagnetic energy through a transmitter shield spanning a full diameter of the transmitter coil, the transmitter shield including a conductive ring having a break so as to prevent a closed 360 degree loop around the ring, conductive fingers projecting radially outward or inward from the ring, and a transmitter ground connection for connecting the ring and the fingers to a transmitter ground. The method can include receiving a magnetic field of the electromagnetic energy into a receiver coil within an implant device in order to inductively couple with the transmitter coil, the received magnetic field driving a current in the receiver coil, and suppressing an electric field emanating from the receiver coil by the current driven in the receiver coil using a receiver shield cupping around the receiver coil, the receiver shield including a conductive annulus having a break so as to prevent a 360 degree closed loop around the annulus, conductive strips projecting radially outward or inward from the annulus, conductive ribs projecting perpendicularly around a circumference of the annulus, and a receiver ground connection connecting the annulus, strips, and ribs to an implant ground for the implant device. This curtails capacitive coupling through electric fields.

The method can include measuring signals from an electrode input that connects from outside to inside the implant device, the measuring occurring during the transmitting, inhibiting, receiving, and suppressing. The suppressing can be enhanced with a ground plane over an end of the cupped receiver shield, the ground plane forming a Faraday cage with the conductive annulus, the conductive strips, and the conductive ribs of the receiver shield. A polymeric, cylindrical housing can enclose the receiver shield and the ground plane.

The method can include directing the magnetic field through a round of ferrite, the receiver coil wrapped around a diameter of the round of ferrite. It can include communicating data through a patch antenna centered within the annulus of the receiver shield, the communicating occurring during the transmitting, inhibiting, receiving, and suppressing. The annulus can be parallel to the receiver coil.

The magnetic inductive coupling apparatus can be a charger system, and the method can further include recharging a battery using the magnetic field-driven current in the receiver coil.

BRIEF DESCRIPTION OF THE DRAWINGS

FIG. 4B is a cross-section of the implant of FIG. 4A.

DETAILED DESCRIPTION

A grounded, capacitive shield is efficient at containing electric fields created by alternating current (AC) voltage of charging coils, both on transmitting (TX) and receiving (RX) coil sides. Each shield can reduce current through tissue, reduce charging noise, and prevent tissue harm.

A gap in a Faraday-cage-like structure around the coils prevents a short circuit loop around each coil and resulting eddy currents that would otherwise impact charging performance. The gap can be filled with an insulator, left as an air gap, or otherwise kept from short circuiting as known in the art.

Figure 1A:
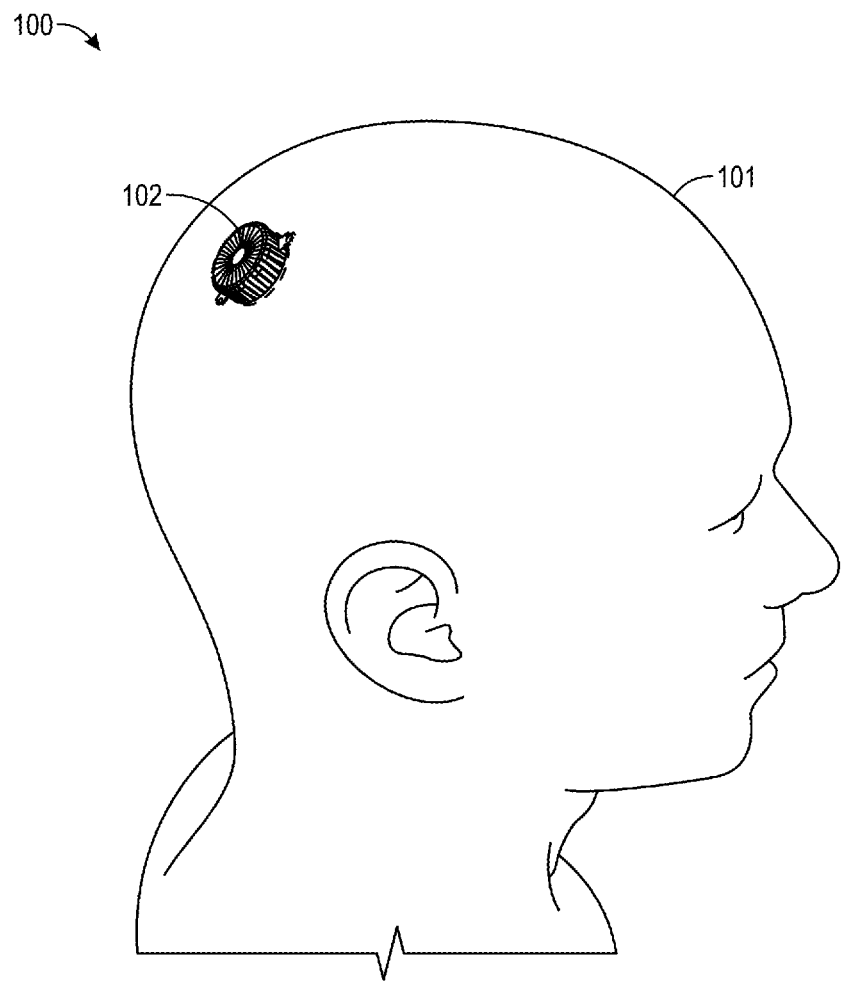
FIG. 1A illustrates a perspective view of an implanted neural device in accordance with an embodiment.

FIG. 1A illustrates a perspective view of an implanted neural device in a subject's head. In system 100, a bore hole in the cranium of subject 101 is filled with cylindrical medical implant 102. Implant 102 is surrounded by tissue, which in this case is the surrounding bone of the cranium and the cerebral cortex of the brain. The cerebral cortex, swimming in cerebral spinal fluid (CSF), is quite conductive, the bone less so. Skin and hair may also cover the implant, further surrounding it with tissue.

The medical implant has a top that faces outward and a bottom that faces inward toward the subject's cerebrum. On the inward side, electrodes come out of implant 102 and extend into the subject's cortex. They pick up tiny voltages or currents, herein referred to as neural signals, that are caused by the brain's synapses firing. The electrodes lead from the cortex into the housing of the implant where amplifiers and analog-to-digital converters connect them to electronics within. The electronics are powered by a battery that is recharged by a wireless charger.

Figure 1B:
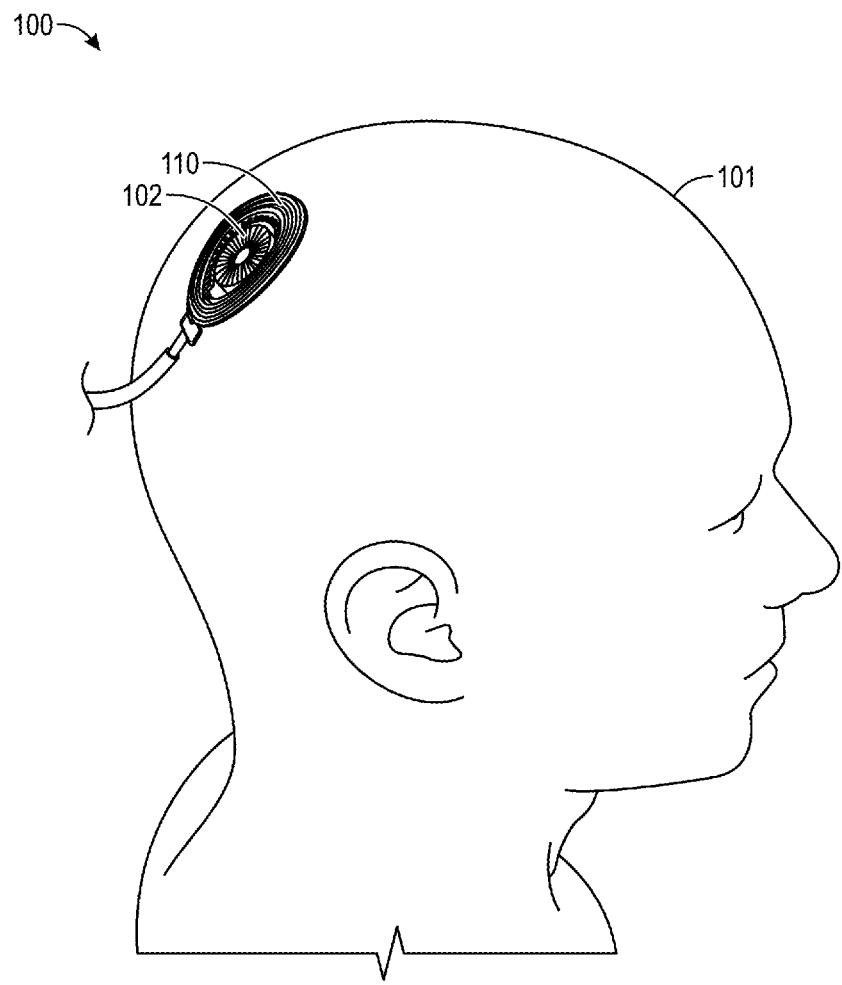
FIG. 1B illustrates a charging coil over the implanted neural device of FIG. 1A.

FIG. 1B illustrates system 100 in which charging coil 110 is applied over neural implant 102, tangentially to the three-dimensional (3D) curvature of the head. As shown, the diameter of charging coil 110 is larger than the diameter of implant 102, yet this may be unnecessary. That is, the diameter of the charging coil may be smaller than, equal to, or larger than that of the implant depending on optimal coil sizes, materials, and locations for wireless power transfer.

The charging coil can be part of a larger device, handheld, worn, or otherwise held in place. For example, the charging coil can be sewn into a wheelchair headrest so that it is placed comfortably for a user. For simplicity of illustration, a simple charging coil is shown.

Figure 2:
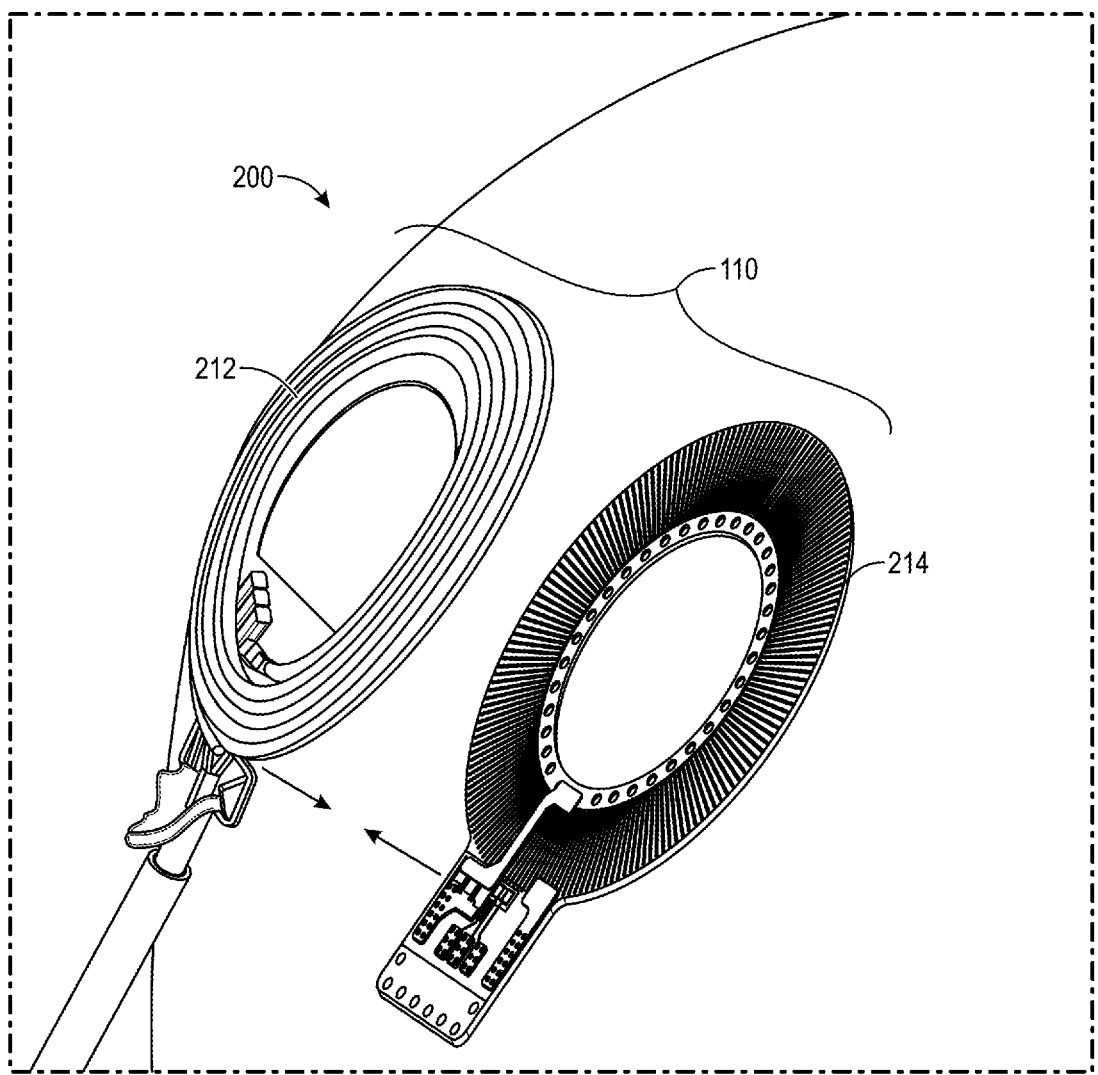
FIG. 2 is an exploded view of a charging coil in accordance with an embodiment.

FIG. 2 is an exploded view of charging coil 100. In assembly 200, charging coil 110 includes transmitter coil 212 with transmitter shield 214 spanning a full diameter of the transmitter coil. That is, transmitter shield 214 has a larger planform than transmitter coil 212 such that no line normal to the head surface passes through the coil without first passing through the shield. That keeps electric fields emanating from transmitter coil 212 from penetrating directly, through a shortest distance, into the patient's head.

Transmitter coil 212 is connected on one end to a ribbon cable through a tab of flexible substrate that juts out from the circumference of the coil. The tab includes connection areas not only for the ribbon cable but also for shield grounding and surface mount capacitors to tune the resonance of the coil.

Figure 3:
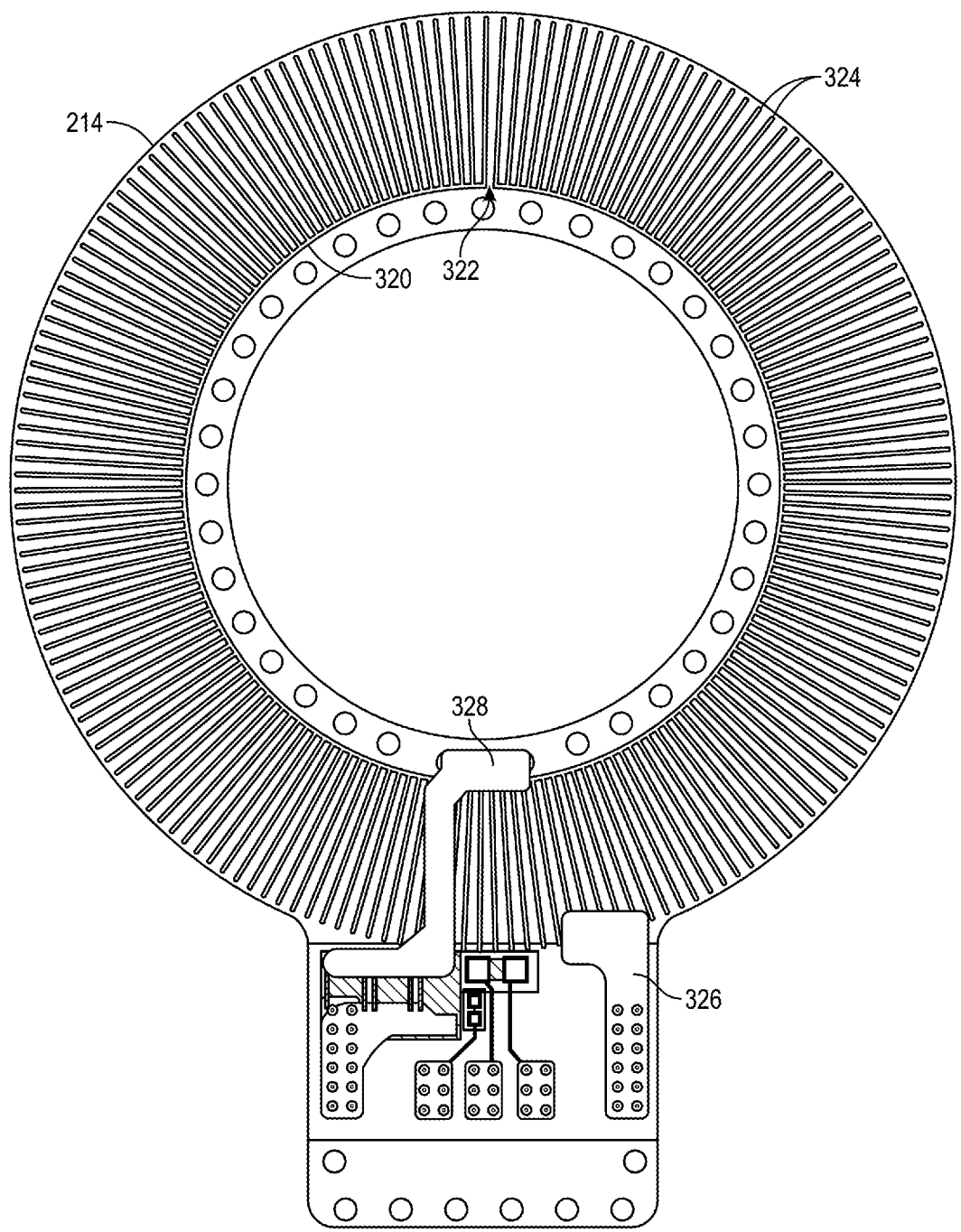
FIG. 3 is a top view of a transmitter shield in accordance with an embodiment.

FIG. 3 is a top view of a transmitter shield in accordance with an embodiment. Transmitter shield 214 is a flexible substrate upon which a pattern of metal foil creates a ring that connects narrow regions of conductor "fingers" and a ground. Conductive ring 320 proceeds all of the way around transmitter shield 214 except for break 322. Break 322 prevents a closed 360 degree loop around ring 320.

Conductive fingers 324 projecting radially outward from the ring to a perimeter of shield 214. The fingers are narrow so as to lessen eddy currents that would otherwise occur in a more continuous shield. In some embodiments, the fingers can project radially inward toward the center of the shield or in other patterns.

Transmitter ground connection 326 connects to a few of fingers 324, through which it connects to conductive ring 320. It is to connect the ring and the fingers to a common transmitter ground. Transmitter ground connection 326 can be tied to a true, earth ground through a relevant connection for the larger charging coil device, such as through a third prong on a power outlet. It may also be left floating with the rest of the transmitter charger to serve as a bulk ground.

Figure 4A:
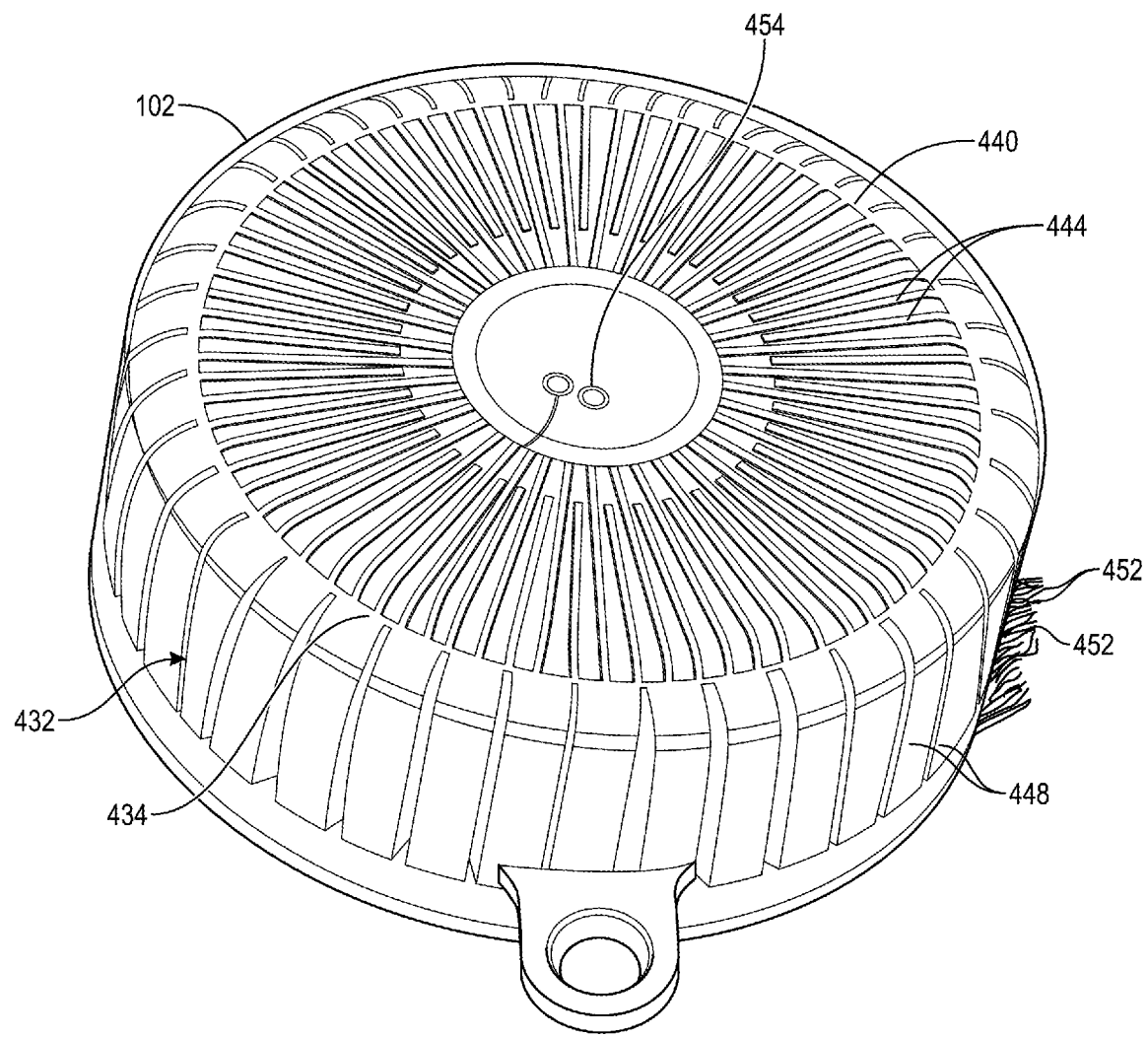
FIG. 4A is a perspective view of an implant in accordance with an embodiment.

FIGS. 4A-4B illustrate an implant in accordance with an embodiment. Neural implant 102 includes cylindrical, non-conductive housing 450 that encloses receiver coil 432 and other electronics. Housing 450 is polymeric so that electromagnetic signals can pass therethrough. The electronics include amplifiers that take amplify voltages or currents from electrodes 452, which run from local tissue outside implant 102 to inside the housing of the implant. The amplifiers are connected to analog-to-digital converters (ADC) that measure the voltages and currents and convert them to digital values. The digital values are then sent to one or more processors mounted on a printed circuit board (PCB) having ground plane 462 in order to be analyzed and classified, volatile or nonvolatile memory for long or short-term storage, multiplexers to be transmitted off board the device and subject, and other components.

The electronics are powered by battery 460, which is recharged through a magnetic field-driven current in the receiver coil as part of a wireless charging system that includes power electronics of recharging circuit 458 and receiver coil 432. Receiver coil 432 is wrapped around a diameter of a round of ferrite 456. The hollow round of ferrite helps direct and guide magnetic fields efficiently through receiver coil 432.

Receiver shield 434 cups around receiver coil 432. That is, the receiver shield surrounds a circumference and an end, at the top in the figure, of the circular coil in a cup-like shape. It does this with narrow metal strips and ribs connected to each other through an annulus.

Receiver shield 434 includes conductive annulus (ring) 440 that progresses almost all of the way around except for a small break so as to prevent a 360 degree closed loop around annulus 440 (see FIG. 4A). Conductive strips 444 project radially inward from annulus 440 and effectively block electric fields emitted axially from the receiver coil. Conductive ribs 448 project outward from annulus 440 and then curve to project perpendicularly from a plane of the annulus. They project around the circumference of annulus 440, forming the sides of an inverted cup shape around receiver coil 432.

Ground plane 462 (see FIG. 4B) effectively caps the cup of receiver shield 434, conductively. Receiver shield 434, with conductive annulus 440, conductive strips 444, and conductive ribs 448 form a Faraday cage with ground plane 462 around receiver coil 432 and the implant's electronics Outside of the receiver coil, ferrite, and receiver shield is BLUETOOTH® patch antenna 454. It is centered within conductive annulus 440 and in a plane parallel to receiver coil 432. The location allows antenna to send and receive data between the electronics within implant 102 and outside networks. Data that can be communicated out can be raw or processed neural data, temperature, relative humidity, and other measurements, diagnostics of the device, and other data. Data communicated in can be for stimulating certain electrodes, data for reprogramming the device itself, and other uses.

Neural signals can be measured by electrodes 452 while an electric field emitted by the transmitter coil is inhibited by the transmitter shield and the electric field emitted by the receiver coil is suppressed. Without the shields, the tissue surrounding the implant would capacitively couple with the coils and rise up and down in voltage at the frequency of the power coil and nearby frequencies due to nonlinear effects. Measurements of tiny microvoltages and microamperes can be made. The shields can allow contemporaneous charging and measurement.

Figure 5:
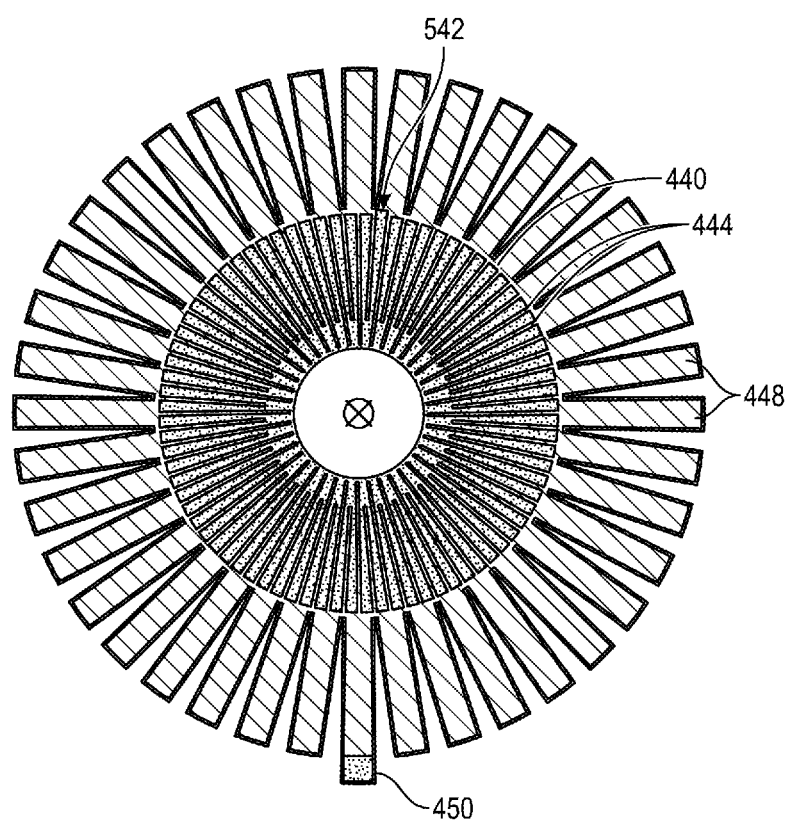
FIG. 5 is a top view of an unfolded receiver shield in accordance with an embodiment.

FIG. 5 is a top view of a receiver shield before it is folded to cup around a receiver coil as in FIGS. 4A-4B. The receiver shield includes conductive annulus 440, the same as in FIG. 4A, with conductive strips 444 projecting inward and conductive ribs 448 projecting outward.

Break 542 in conductive annulus 440 is shown at the 12 o'clock position in the figure. Break 542 has a small amount of insulation in the break in the form of a conformal coating. Opposite the break at the 6 o'clock position at the bottom of the figure, receiver ground connection 450 is an extended tab portion of one of metal ribs. The receiver ground connection is configured to connect conductive annulus 440, conductive strips 444, and conductive ribs 448 to an implant ground for the implant device. Because the implant device is surrounded by and electrically isolated from tissue, its ground is effectively a floating ground with respect to earth ground.

In some embodiments, a tighter or looser pattern of strips and ribs is used, depending on requirements for the resulting Faraday cage that encompasses the receiver coil. Zig zag or other patterns of metal, with narrow features in order to minimize eddy currents, can also serve the same purpose.

Figure 6:
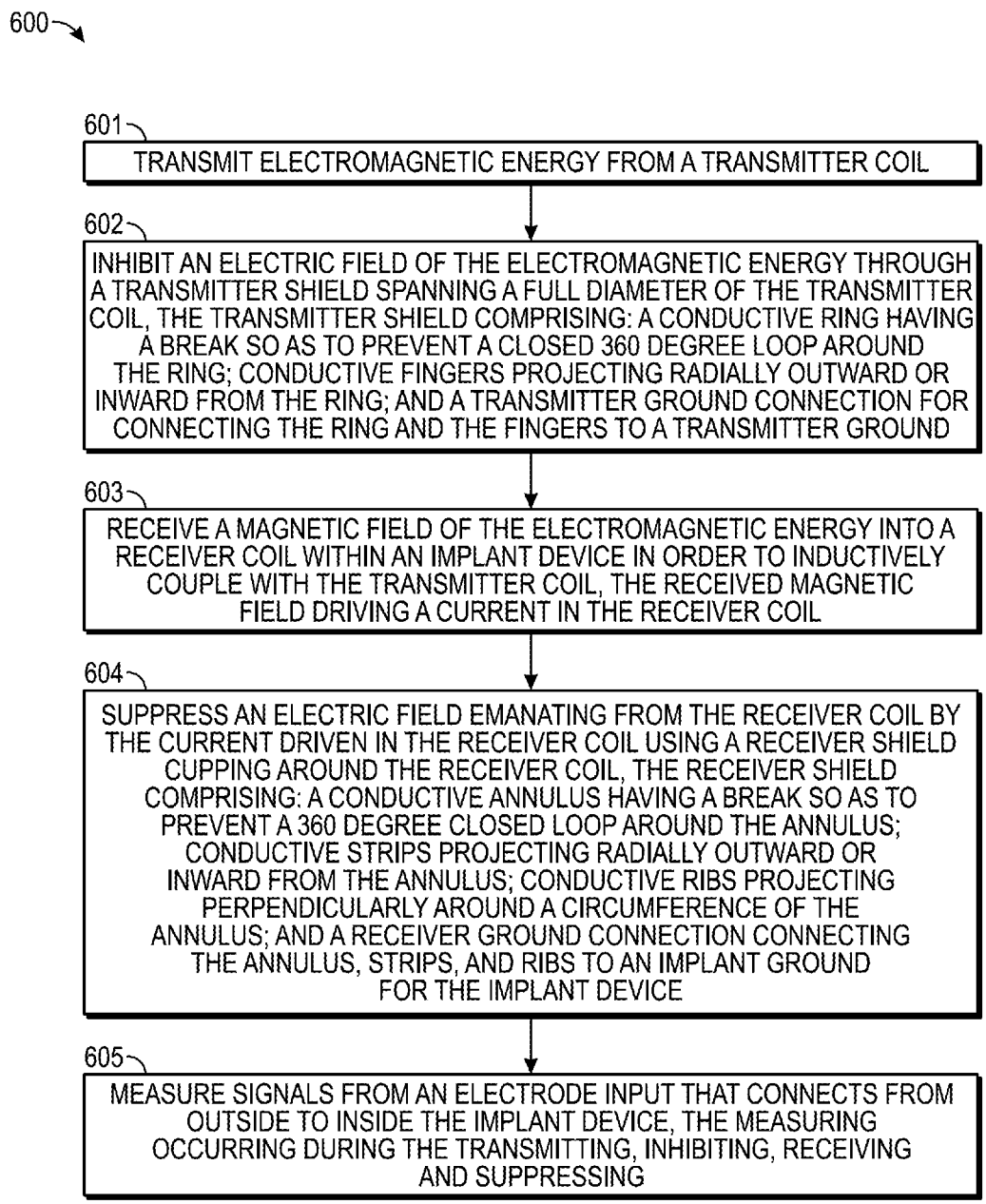
FIG. 6 is a flowchart illustrating an embodiment in accordance with the present invention.

FIG. 6 is a flowchart of a process 600 in accordance with an embodiment. In operation 601, electromagnetic energy is transmitted from a transmitter coil. In operation 602, an electric field of the electromagnetic energy is inhibited by going through a transmitter shield spanning a full diameter of the transmitter coil, the transmitter shield comprising a conductive ring having a break so as to prevent a closed 360 degree loop around the ring, conductive fingers projecting radially outward or inward from the ring, and a transmitter ground connection for connecting the ring and the fingers to a transmitter ground. In operation 603, a magnetic field of the electromagnetic energy is received into a receiver coil within an implant device in order to inductively couple with the transmitter coil, the received magnetic field driving a current in the receiver coil. In operation 604, an electric field emanating from the receiver coil by the current driven in the receiver coil is suppressed using a receiver shield cupping around the receiver coil, the receiver shield comprising a conductive annulus having a break so as to prevent a 360 degree closed loop around the annulus, conductive strips projecting radially outward or inward from the annulus, conductive ribs projecting perpendicularly around a circumference of the annulus, and a receiver ground connection connecting the annulus, strips, and ribs to an implant ground for the implant device. In operation 605, signals from an electrode input that connects from outside to inside the implant device are measured, the measuring occurring during the transmitting, inhibiting, receiving, and suppressing.

It should be appreciated that a thin-foil wireless power coil can be connected with electronics that power one or more microprocessors/processing devices that can further be a component of the overall apparatuses. Such processing devices can be communicatively coupled to a non-volatile memory device via a bus. The non-volatile memory device may include any type of memory device that retains stored information when powered off. Non-limiting examples of the memory device include electrically erasable programmable read-only memory ("ROM"), flash memory, or any other type of non-volatile memory. In some aspects, at least some of the memory device can include a non-transitory medium or memory device from which the processing device can read instructions. A non-transitory computer-readable medium can include electronic, optical, magnetic, or other storage devices capable of providing the processing device with computer-readable instructions or other program code. Non-limiting examples of a non-transitory computer-readable medium include (but are not limited to) magnetic disk(s), memory chip(s), ROM, random-access memory ("RAM"), an ASIC, a configured processor, optical storage, and/or any other medium from which a computer processor can read instructions. The instructions may include processor-specific instructions generated by a compiler and/or an interpreter from code written in any suitable computer-programming language, including, for example, C, C++, C#, Java, Python, Perl, JavaScript, etc.

While the above description describes various embodiments of the invention and the best mode contemplated, regardless how detailed the above text, the invention can be practiced in many ways. Details of the system may vary considerably in its specific implementation, while still being encompassed by the present disclosure. As noted above, particular terminology used when describing certain features or aspects of the invention should not be taken to imply that the terminology is being redefined herein to be restricted to any specific characteristics, features, or aspects of the invention with which that terminology is associated. In general, the terms used in the following claims should not be construed to limit the invention to the specific examples disclosed in the specification, unless the above Detailed Description section explicitly defines such terms. Accordingly, the actual scope of the invention encompasses not only the disclosed examples, but also all equivalent ways of practicing or implementing the invention under the claims.

The teachings of the invention provided herein can be applied to other systems, not necessarily the system described above. The elements and acts of the various examples described above can be combined to provide further implementations of the invention. Some alternative implementations of the invention may include not only additional elements to those implementations noted above, but also may include fewer elements. Further any specific numbers noted herein are only examples; alternative implementations may employ differing values or ranges, and can accommodate various increments and gradients of values within and at the boundaries of such ranges.

References throughout the foregoing description to features, advantages, or similar language do not imply that all of the features and advantages that may be realized with the present technology should be or are in any single embodiment of the invention. Rather, language referring to the features and advantages is understood to mean that a specific feature, advantage, or characteristic described in connection with an embodiment is included in at least one embodiment of the present technology. Thus, discussion of the features and advantages, and similar language, throughout this specification may, but do not necessarily, refer to the same embodiment. Furthermore, the described features, advantages, and characteristics of the present technology may be combined in any suitable manner in one or more embodiments. One skilled in the relevant art will recognize that the present technology can be practiced without one or more of the specific features or advantages of a particular embodiment. In other instances, additional features and advantages may be recognized in certain embodiments that may not be present in all embodiments of the present technology.

What is claimed is:

1. A capacitively shielded magnetic inductive coupling apparatus for medical implants, the apparatus comprising:
   a transmitter coil;
   a transmitter shield spanning a full diameter of the transmitter coil, the transmitter shield comprising:
      a conductive ring having a break so as to prevent a closed 360 degree loop round the ring;
      conductive fingers projecting radially outward or inward from the ring; and
      a transmitter ground connection for connecting the ring and the fingers to a transmitter ground;
   a receiver coil within an implant device and configured to inductively couple through magnetic fields with the transmitter coil; and
   a receiver shield cupping around the receiver coil, the receiver shield comprising:

a conductive annulus having a break so as to prevent a 360 degree closed loop around the annulus;

conductive strips projecting radially outward or inward from the annulus;

conductive ribs projecting perpendicularly around a circumference of the annulus; and a receiver ground connection connecting the annulus, strips, and ribs to an implant ground for the implant device;

wherein the transmitter shield and the receiver shield are configured to curtail capacitive coupling through electric fields to tissue around the implant device.

2. The apparatus of claim 1 further comprising:

an electrode input that connects from outside to inside the implant device.

3. The apparatus of claim 1 further comprising:

a ground plane over an end of the cupped receiver shield and forming a Faraday cage with the conductive annulus, the conductive strips, and the conductive ribs of the receiver shield.

4. The apparatus of claim 3 further comprising:

a polymeric, cylindrical housing around the receiver shield and the ground plane.

5. The apparatus of claim 3 further comprising:

a round of ferrite, the receiver coil wrapped around a diameter of the round of ferrite.

6. The apparatus of claim 1 further comprising:

a patch antenna centered within the conductive annulus of the receiver shield, the patch antenna configured for data communications.

7. The apparatus of claim 1 wherein the conductive fingers of the transmitter shield project only outward from the ring.

8. The apparatus of claim 1 wherein the annulus is in a plane parallel to the receiver coil.

9. The apparatus of claim 1 wherein the magnetic inductive coupling apparatus is a charger system, the apparatus further comprising:

a recharging circuit configured to receive power from the receiver coil and charge battery.

10. The apparatus of claim 1 further comprising:

insulation within the break of the conductive ring or the break of the conductive annulus.

11. The apparatus of claim 1 wherein the conductive annulus of the receiver coil is made from a biocompatible metal selected from the group consisting of gold, platinum, silver, tantalum, and titanium.

12. The apparatus of claim 1 wherein the implant device is implanted within tissue of a subject.

13. A method of capacitively shielding a magnetic inductive coupling apparatus for medical implants, the method comprising:

transmitting electromagnetic energy from a transmitter coil;

inhibiting an electric field of the electromagnetic energy through a transmitter shield spanning a full diameter of the transmitter coil, the transmitter shield comprising:

a conductive ring having a break so as to prevent a closed 360 degree loop around the ring;

conductive fingers projecting radially outward or inward from the ring; and a transmitter ground connection for connecting the ring and the fingers to a transmitter ground;

receiving a magnetic field of the electromagnetic energy into a receiver coil within an implant device in order to inductively couple with the transmitter coil, the received magnetic field driving a current in the receiver coil; and suppressing an electric field emanating from the receiver coil by the current driven in the receiver coil using a receiver shield cupping around the receiver coil, the receiver shield comprising:

a conductive annulus having a break so as to prevent a 360 degree closed loop around the annulus;

conductive strips projecting radially outward or inward from the annulus;

conductive ribs projecting perpendicularly around a circumference of the annulus; and a receiver ground connection connecting the annulus, strips, and ribs to an implant ground for the implant device;

thereby curtailing capacitive coupling through electric fields.

14. The method of claim 13 further comprising:

measuring signals from an electrode input that connects from outside to inside the implant device, the measuring occurring during the transmitting, inhibiting, receiving, and suppressing.

15. The method of claim 13 wherein the suppressing is enhanced with a ground plane over an end of the cupped receiver shield, the ground plane forming a Faraday cage with the conductive annulus, the conductive strips, and the conductive ribs of the receiver shield.

16. The method of claim 15 wherein a polymeric, cylindrical housing encloses the receiver shield and the ground plane.

17. The method of claim 15 further comprising:

directing the magnetic field through a round of ferrite, the receiver coil wrapped around a diameter of the round of ferrite.

18. The method of claim 13 further comprising:

communicating data through a patch antenna centered within the annulus of the receiver shield, the communicating occurring during the transmitting, inhibiting, receiving, and suppressing.

19. The method of claim 13 wherein the annulus is parallel to the receiver coil.

20. The method of claim 13 wherein the magnetic inductive coupling apparatus is a charger system, the method further comprising:

recharging a battery using the magnetic field-driven current in the receiver coil.

* * * * *